United States Patent [19]

Layton et al.

[11] 4,301,812
[45] Nov. 24, 1981

[54] MIDSTREAM SAMPLING DEVICE

[75] Inventors: Terry N. Layton, Arlington Heights; Carl J. Steigerwald, Wauconda, both of Ill.

[73] Assignee: The Kendall Company, Boston, Mass.

[21] Appl. No.: 102,673

[22] Filed: Dec. 12, 1979

[51] Int. Cl.³ .......................... A61B 10/00; G01N 1/10
[52] U.S. Cl. .................................. 128/761; 73/863.52; 128/762
[58] Field of Search ............. 73/421 R; 128/761, 762, 128/295; 4/144.3

[56] References Cited

U.S. PATENT DOCUMENTS

| | | | |
|---|---|---|---|
| 3,635,091 | 1/1972 | Linzer et al. | 73/421 R |
| 3,680,543 | 8/1972 | Cox | 128/295 X |
| 3,750,647 | 8/1973 | Gleason et al. | 128/761 |
| 3,750,648 | 8/1973 | Gleason et al. | 128/761 |
| 3,859,671 | 1/1975 | Tomasello | 128/762 X |
| 3,929,412 | 12/1975 | Villari | 128/295 X |
| 4,106,490 | 8/1978 | Spilman et al. | 128/761 |

*Primary Examiner*—Daniel M. Yasich
*Attorney, Agent, or Firm*—Powell L. Sprunger

[57] ABSTRACT

A midstream sampling device comprising, a housing having a chamber, a distal outer mouth defining an outer port, an inner mouth in the chamber defining an inner port, and an outlet opening. The housing has a first cavity communicating between the inner port and the outlet opening, and a second cavity at least partially below the inner mouth and communicating with the outer port. The housing has an elongated depending post having a channel, and an upper aperture communicating with at least one of the cavities. The device also has a receptacle having a chamber communicating with the outlet opening.

14 Claims, 15 Drawing Figures

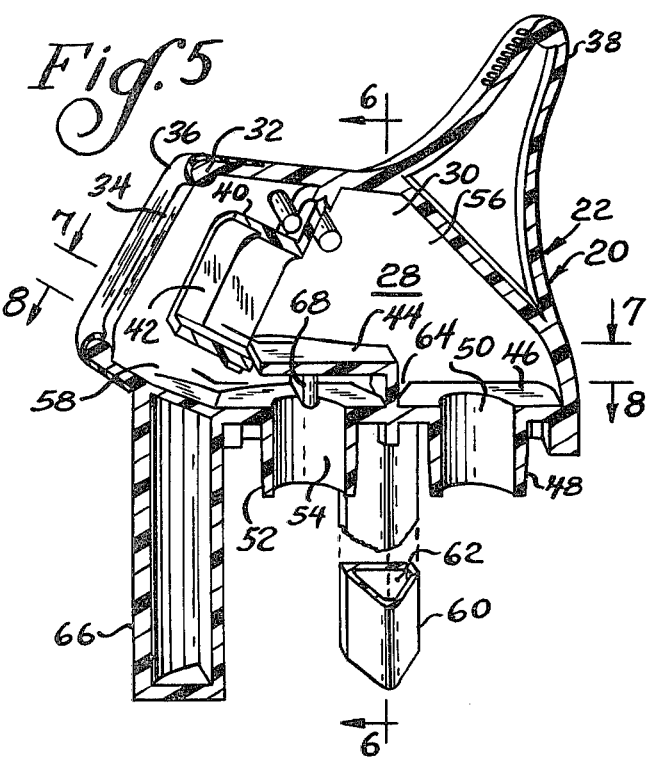
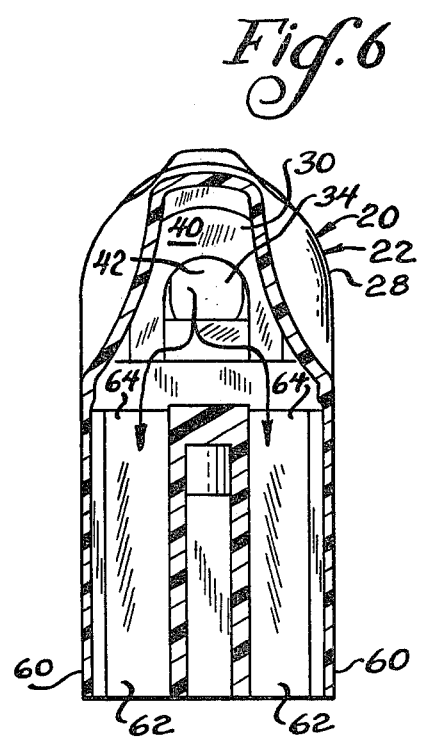
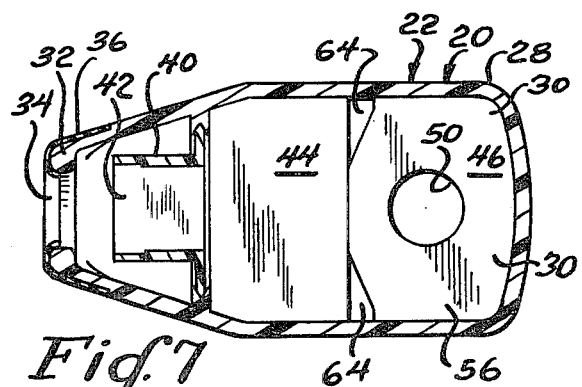
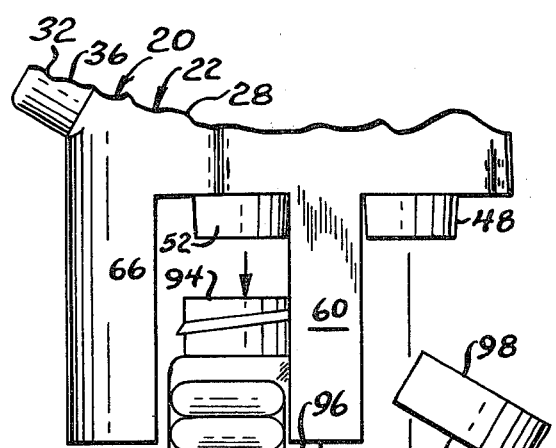
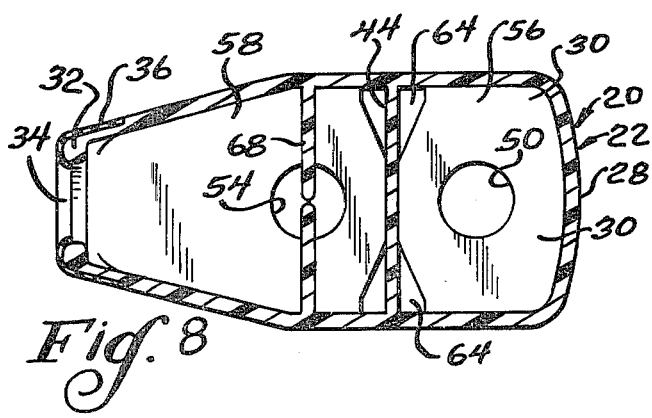

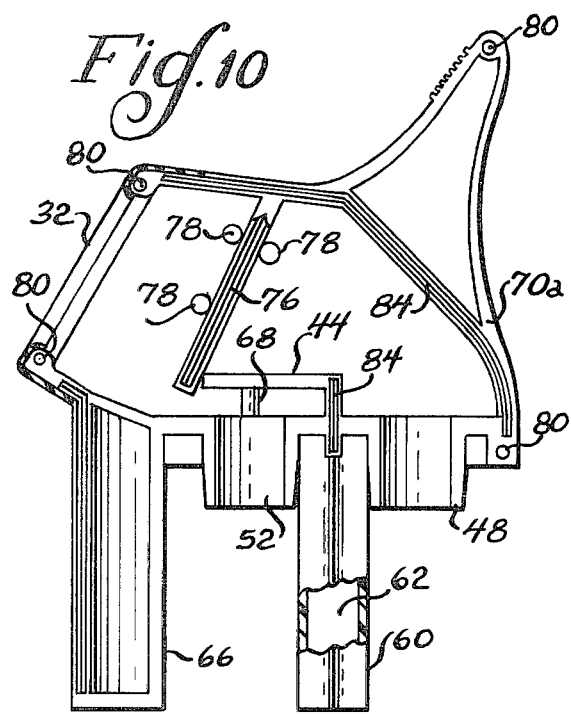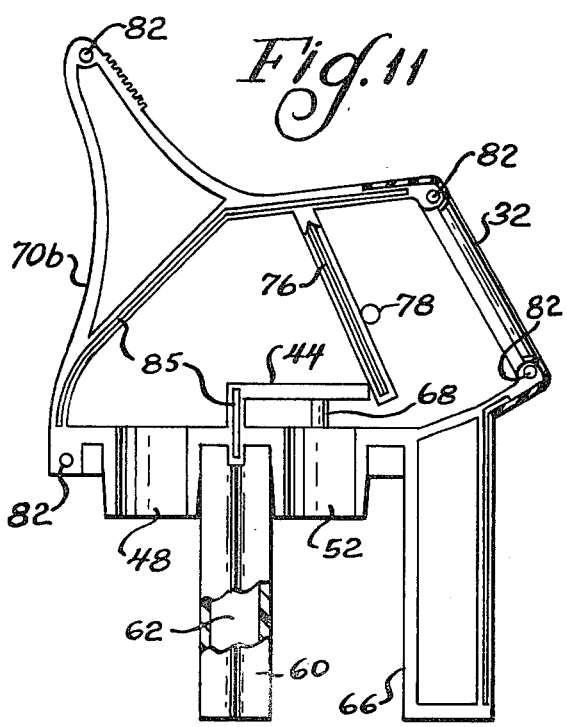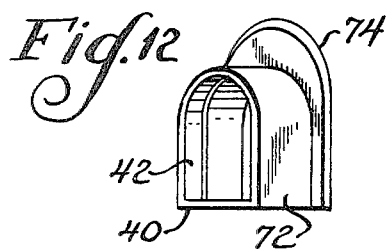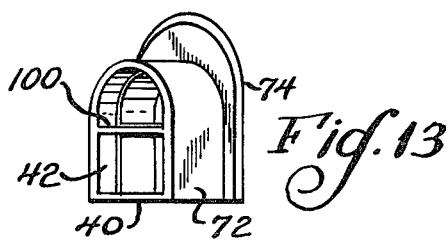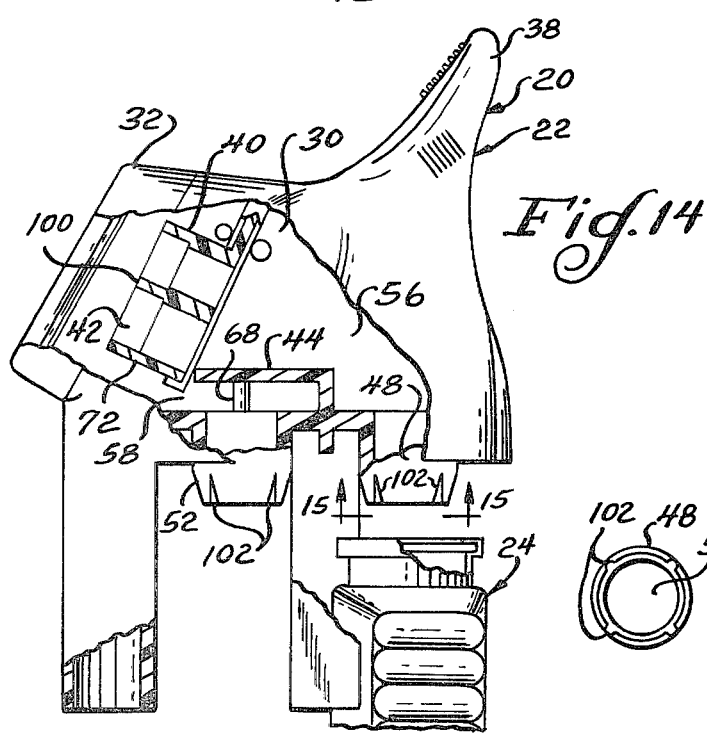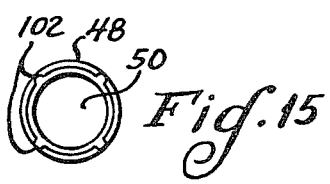

MIDSTREAM SAMPLING DEVICE

BACKGROUND OF THE INVENTION

The present invention relates to midstream sampling devices.

It is frequently desirable to obtain a clean sample of urine from a patient for purposes of analysis. A number of devices have been proposed for obtaining such a sample from male patients, but it has been more difficult to obtain a clean sample of urine from a female patient. A clean sample requires that the urine not touch a non-sterile area, such as the labia in the case of female patients. Also, it is desirable to collect the midstream portion of the urine discharge, since the initial portion of the discharge may become contaminated due to retrograde contamination in the urethra.

SUMMARY OF THE INVENTION

A principal feature of the present invention is the provision of an improved device for collecting the midstream portion of a urine discharge from a female patient.

The device of the present invention comprises, a housing having a chamber, a distal outer mouth defining an outer port, and an inner mouth in the chamber defining an inner port generally aligned with the outer port. The housing has a first lower proximal outlet opening, and a first proximal cavity communicating between the inner port and the first outlet opening. The housing has a second lower distal outlet opening, and a second distal cavity at least partially below the inner mouth and communicating between the outer port and the second outlet opening. The housing has a pair of depending elongated posts adjacent opposed sides of the housing intermediate the first and second outlet openings, with the ports defining a pair of channels extending through the posts, and defining a pair of apertures communicating between the channels and a lower portion of the first and second cavities. The device has a first receptacle releasably attached to the housing and having a chamber in the first receptacle, and a second receptacle releasably attached to the housing and having a chamber in the second receptacle.

A feature of the present invention is that the outer mouth may be positioned inside a labia of a patient to capture a urine sample without contamination by the labia.

Another feature of the invention is that the initial portion of the discharge passes through the second cavity to the second outlet opening due to its relatively low velocity.

Yet another feature of the invention is that the second receptacle communicates with the second outlet opening to capture the initial portion of the urine discharge.

A further feature of the invention is that the midstream portion of the discharge passes through the inner mouth due to its relatively high velocity.

Still another feature of the invention is that the first receptacle communicates with the first outlet opening to capture the midstream portion of the urine discharge.

A further feature of the invention is that overflow of liquid from the first or second receptacle passes through the apertures into the posts and out of the housing.

A feature of the present invention is that the overflow liquid is disposed of through the posts without wetting the first or second receptacle.

Further features will become more fully apparent in the following description of the embodiments of this invention and from the appended claims.

DESCRIPTION OF THE DRAWINGS

In the drawings:

FIG. 5 is a fragmentary sectional view of the housing of FIG. 1;

FIG. 6 is a sectional view taken substantially as indicated along the line 6—6 of FIG. 5;

FIG. 7 is a sectional view taken substantially as indicated along the line 7—7 of FIG. 5;

FIG. 8 is a sectional view taken substantially as indicated along the line 8—8 of FIG. 5;

FIG. 9 is a fragmentary elevational view of the housing of FIG. 1 and a pair of receptacles which are releasably attached to the housing;

FIGS. 10 and 11 are elevational views, partly broken away, of preformed halves which may be assembled into the housing of FIG. 1;

FIG. 12 is a perspective view of an inner mouth for the housing of FIGS. 10 and 11;

FIG. 13 is a perspective view of another embodiment of the mouth of FIG. 12;

FIG. 14 is a fragmentary elevational view illustrating the device with the mouth of FIG. 13; and FIG. 15 is a lower view taken substantially as indicated along the line 15—15 of FIG. 14.

DESCRIPTION OF THE PREFERRED EMBODIMENTS

Figure 1:
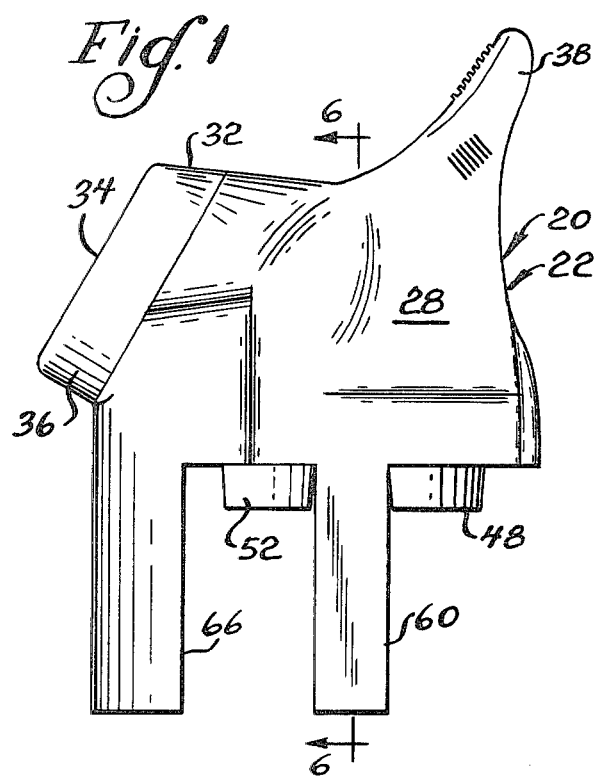
FIG. 1 is a side elevational view showing a housing of a midstream sampling device of the present invention.
Figure 2:
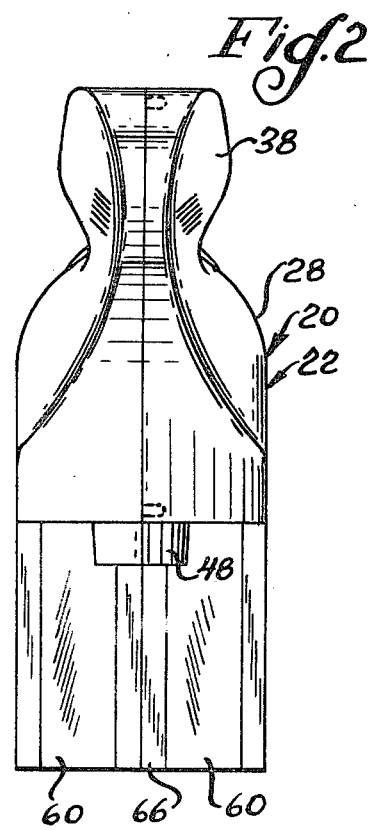
FIG. 2 is a rear elevational view of the housing of FIG. 1.
Figure 3:
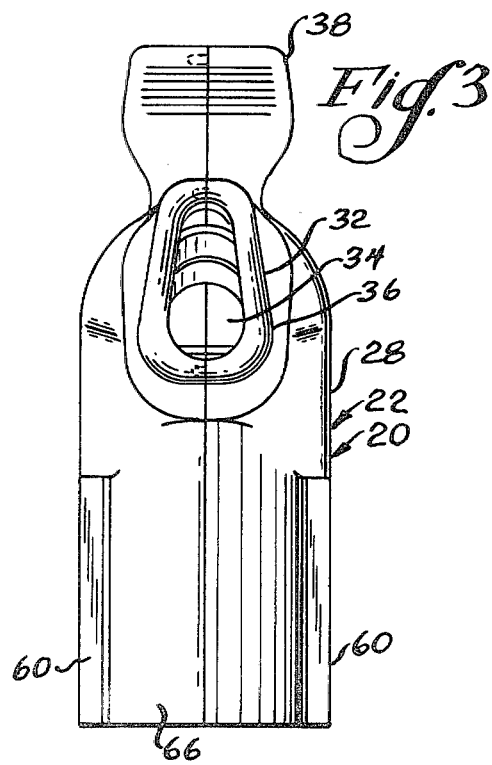
FIG. 3 is a front elevational view of the housing of FIG. 1.
Figure 4:
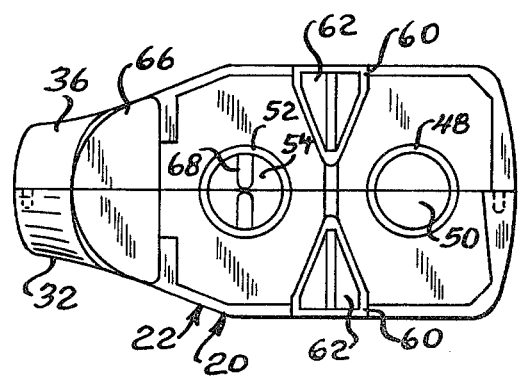
FIG. 4 is a lower plan view of the housing of FIG. 1.

Referring now to FIGS. 1-9, there is shown a midstream sampling device generally designated 20 having a housing 22 and first and second receptacles 24 (FIG. 14) and 26 (FIG. 9), respectively. The housing 22 has an outer wall 28 defining an internal chamber 30, and a distal outer oval mouth 32 defining an outer port 34. In a preferred form, the outer wall 28 is recessed adjacent the outer mouth 32 to receive a resilient bumper member 36 extending peripherally around the outer port 34, as shown. The housing 22 has an outwardly and upwardly extending proximal portion defining a handle 38 for the device during use. The housing may be made from a suitable material, such as plastic, and the bumper member 36 may be constructed from rubber.

The housing 22 has an inner mouth 40 generally aligned with the outer mouth 32 and defining an inner port 42. The housing has a ledge 44 extending from a lower portion of the inner mouth 40 to a central portion of a lower wall 46 of the housing. The lower wall 46 has a first proximal depending tubular extension 48 defining a first proximal outlet opening 50, and a more distal second depending tubular extension 52 defining a second distal outlet opening 54. As shown, the inner mouth 40 and ledge 44 define a first cavity 56 extending between the inner port 42 and first outlet opening 50, and a second cavity 58 partially below the inner mouth 40 and communicating between the outer port 34 and the second outlet opening 54.

The housing 22 has a pair of hollow equal-length depending posts 60 located adjacent opposed sides of the housing and located intermediate the first and second outlet openings 50 and 54, respectively. The posts 60 each have a channel 62 extending through the posts 60, with the lower wall 46 defining respective apertures 64 communicating with the channels 62. As shown, the ledge 44 has a proximal end portion separating the apertures 64 into a first portion communicating with the first cavity 56 and a second portion communicating with the second cavity 58. The housing 22 has a distal depending post 66 having a length approximately equal to the length of the posts 60 and located adjacent the second outlet opening 54. The posts 60 and 66 may be utilized to support the device 20 on a suitable flat surface when not in use. Also, as shown, the ledge 44 has a depending stop member 68 extending across the housing 22 in the second cavity 58 centrally above the second outlet opening 54.

With reference to FIGS. 10–12, the housing 22 of the present invention may be constructed in a simplified manner from first and second half members 70a and 70b, respectively. As shown, the inner mouth 40 has a somewhat annular mouth member 72 defining the port 42, and an outwardly directed flange 74 extending from the mouth member 72. The half members 70a and b have a pair of slanted grooves 76 to receive the flange 74 of the inner mouth 40, and have a plurality of inwardly directed pegs 78 to hold the flange 74 of the inner mouth 40 in place. The first half member 70a has a plurality of apertures 80 to receive a plurality of associated pegs 82 extending from the second half member 70b. Also, the first half member 70a has a pair of grooves 84 to receive a corresponding pair of ridges 85 on the second half member 70b. Thus, the inner mouth 40 may be positioned on one of the half members 70a or 70b, and the half members 70a and b may be closed about the inner mouth, and may be cemented in place to form the housing 22 through use of a suitable adhesive.

With reference to FIG. 9, the first receptacle 24 has a chamber 86, an upper threaded neck 88, and a tapered wall 90. The second receptacle 26 also has a chamber 92, an upper threaded neck 94, and a tapered wall 96. The first receptacle 24 may be releasably attached to the first tubular extension 48 which is snugly received in the first receptacle neck 88, such that the inner port 42 communicates with the first receptacle chamber 86 through the first cavity 56 and first outlet opening 50. The second receptacle 26 may be releasably attached to the second tubular extension 52 which is snugly received in the neck 94 of the second receptacle 26, with the outer port 34 communicating with the chamber 92 of the second receptacle 26 through the second cavity 58 and second outlet opening 54. With reference to FIGS. 1–9, the aligned posts 60 have a generally triangular shape in cross-section, with the vertices of the triangles being directed toward each other. Thus, the first and second receptacles 24 and 26 may be secured to the housing 22 with the posts 60 located intermediate the opposed sides of the receptacles 24 and 26, and with the walls 90 and 96 of the first and second receptacles 24 and 26, respectively, facing toward the posts 60. Also, the second receptacle is secured to the housing 22 at a location intermediate the distal post 66 and the posts 60. The receptacles 24 and 26 have a length slightly less than the posts 60 and 66 when they are secured to the housing 22, such that the housing 22 rests upon the posts 60 and 66 when it is placed on a surface, with the receptacles 24 and 26 being frictionally engaged to the first and second tubular extensions 48 and 52, respectively.

With reference to FIG. 9, the first and second receptacles 24 and 26 may have a suitable cap 98 which may be secured to the necks of the receptacles by the threads on the necks.

In use, the first and second receptacles 24 and 26 are secured to the first and second tubular extensions 48 and 52 of the housing 22. Next, the labia are spread by the user, and the outer mouth 32 is placed within the labia at a location with the outer port 34 positioned to receive urine passing from the urethra, with the bumper member 36 providing comfort for the patient in this configuration. The sampling device 20 is positioned by the patient while sitting upon the toilet. When urination has started, the initial portion of the urine discharge passes through the outer port 34 into the second cavity 58, due to its relatively low velocity, and the stop member 68 directs the initial portion of the discharge through the second outlet opening 54 into the chamber 92 of the second receptacle 26. In the event that the second receptacle 26 overflows, the overflowing liquid passes from the second outlet opening 54 to the apertures 64, and through the channels 62 of the posts 60 into the toilet.

As the discharge continues, the midstream portion thereof passes through the inner port 42 due to its relatively large velocity, and through the first cavity 56 and first outlet opening 50 into the chamber 86 of the first receptacle 24 for collection therein. In the event that the first receptacle 24 overflows, the overflowing liquid passes from the first outlet opening 50 to the apertures 64, and through the channels 62 of the posts 60 into the toilet. Thus, overflowing urine from either of the cavities 56 or 58 is directed by the posts 60 into the toilet to prevent wetting of the outside of the receptacles in the event of an overflow condition. Also, the initial portion of the discharge, which may be contaminated due to retrograde contamination in the urethra, is collected in the second receptacle 26 which may be discarded, if desired. The clean midstream portion of the discharge is collected in the first receptacle 24, and a cap 98 may be secured to the top of the first receptacle 24 to save the midstream specimen for subsequent analysis.

Another embodiment of the present invention is illustrated in FIGS. 13–15, in which like reference numerals designate like parts. In this embodiment, the mouth member 72 has a web 100 extending across the inner port 42. Also, the first and second tubular extensions 48 and 52 may have external bosses 102 to facilitate the frictional engagement between the tubular extensions and the receptacles. In other respects, the device of FIGS. 13–15 is similar to the device previously described in connection with FIGS. 1–12.

The foregoing detailed description is given for clearness of understanding only, and no unnecessary limitations should be understood therefrom, as modifications will be obvious to those skilled in the art.

We claim:

1. A midstream sampling device for collecting the midstream portion of a urine discharge from a female patient, comprising: a housing defining a chamber therewithin, said housing being structured to be supported on a horizontal surface when not in use; means defining an outer port at one end of said housing, said port having a generally oval shape and being configured to be placed against the labia of a female and receive urine passing from the uretha; means defining an inner port within said chamber, said inner port being smaller than said outer port and being arranged adjacent thereto to receive the midstream portion of a urine discharge; means defining a first cavity within said housing and including a portion of said housing, said first cavity being connected to and in fluid communication with said inner port for initial collection of the midstream discharge; a first outlet port within said first cavity through which the midstream discharge flows; a receptacle detachably connected to said first outlet port for receiving the midstream discharge from said first cavity; means defining a second cavity and including another portion of said housing, said second cavity arranged to receive the initial portion of a urine discharge through said outer port, from the lower portion of the space between said outer port and said inner port; and means defining at least one overflow aperture within said first cavity whereby, during use of said sampling device and upon filling of said receptacle, excess urine within said first cavity will drain from said first cavity through said aperture.

2. The device of claim 1 wherein said housing further includes a handle thereon, at an end opposite said outer port, to facilitate manual positioning of said device to receive a urine discharge.

3. The device of claim 1 wherein said means defining at least one overflow aperture comprises a pair of apertures formed in said first and second cavities, each aperture communicating with both of said cavities thereby to receive a urine discharge overflow from either or both of said cavities, said device further comprising a pair of elongated, depending posts, one for each aperture and surrounding its corresponding aperture, each said post being hollow and having an open channel defined therethrough to direct a urine discharge overflow out of said sampling device.

4. The device of claim 3 wherein said second cavity further includes a second outlet port through which the initial portion of a urine discharge flows, said device further comprising a second receptacle detachably connected to said second outlet port for receiving the initial portion of a urine discharge from said second cavity.

5. The device of claim 4 wherein the posts are located intermediate the sides of the first and second receptacles when the receptacles are attached to the housing.

6. The device of claim 5 wherein the posts have a generally triangular shape in cross section.

7. The device of claim 6 wherein vertices of the triangular shaped posts are directed toward each other.

8. The device of claim 5 wherein the housing includes an elongated third depending post, and in which the second receptacle is located intermediate the pair of posts and the third post when the second receptacle is attached to the housing, the lower ends of all three posts being configured to support the housing upright on a horizontal surface when the device is not in use.

9. The device of claim 4 wherein the first and second receptacles include upper necks, and in which the housing has a pair of spaced depending tubular extensions defining said first and second outlet openings, said necks releasably engaging said tubular extensions when the first and second receptacles are attached to the housing.

10. The device of claim 4 wherein said apertures are located intermediate the first and second openings.

11. The device of claim 10 including a stop member extending over the second outlet opening separating the second cavity over the second outlet opening and intermediate the outer port and said apertures.

12. The device of claim 4 wherein the housing includes a ledge extending from a lower portion of said inner port and separating said first and second cavities.

13. The device of claim 12 wherein said housing includes a lower wall defining the apertures and said first and second outlet openings.

14. The device of claim 13 wherein said ledge extends to said lower wall across said apertures, said ledge separating said apertures into a first portion connected to the first cavity and a second portion connected to said second cavity.

* * * * *